United States Patent
Forstein et al.

(10) Patent No.: US 10,631,934 B2
(45) Date of Patent: Apr. 28, 2020

(54) IMAGE AND LASER GUIDED CONTROL OF CUTTING USING A ROBOTIC SURGICAL SYSTEM

(71) Applicant: THINK SURGICAL, INC., Fremont, CA (US)

(72) Inventors: Micah Forstein, Fremont, CA (US); Justin Eskesen, Fremont, CA (US); Joel Zuhars, Fremont, CA (US)

(73) Assignee: Think Surgical Inc., Fremont, CA (US)

( * ) Notice: Subject to any disclaimer, the term of this patent is extended or adjusted under 35 U.S.C. 154(b) by 162 days.

(21) Appl. No.: 15/542,675

(22) PCT Filed: Jan. 14, 2016

(86) PCT No.: PCT/US2016/013343
§ 371 (c)(1),
(2) Date: Jul. 11, 2017

(87) PCT Pub. No.: WO2016/115306
PCT Pub. Date: Jul. 21, 2016

(65) Prior Publication Data
US 2018/0263697 A1 Sep. 20, 2018

Related U.S. Application Data (60) Provisional application No. 62/103,945, filed on Jan. 15, 2015.

(51) Int. Cl.
*A61B 34/10* (2016.01)
*A61B 34/30* (2016.01)
(Continued)

(52) U.S. Cl.
CPC ............. *A61B 34/10* (2016.02); *A61B 6/032* (2013.01); *A61B 17/1703* (2013.01);
(Continued)

(58) Field of Classification Search
CPC ............. A61B 5/4509; A61B 2034/104; A61F 2002/30948; A61F 2002/4633; G16H 30/00; G16H 30/20
See application file for complete search history.

(56) References Cited

U.S. PATENT DOCUMENTS 5,274,565 A * 12/1993 Reuben ............... A61F 2/30942
700/182
5,824,085 A * 10/1998 Sahay ................. A61F 2/30942
128/898
(Continued)

FOREIGN PATENT DOCUMENTS

| WO | 2013174801 A2 | 11/2013 |
| WO | 2014159924 A1 | 10/2014 |

OTHER PUBLICATIONS

Coles, M.E. et al., "The Use of Attenuation Standards for CT Scanning", 1995 SCA Conference Paper No. 9513, 12 pages, 1995.
(Continued)

*Primary Examiner* — David W Bates
(74) *Attorney, Agent, or Firm* — Blue Filament Law PLLC (57) ABSTRACT

A process and system for computer assisted orthopedic procedure is provided with a plurality of options to plan, execute, and monitor the creation of a cavity to receive a prosthetic based on clinical needs and pre-operative imaging data. A phantom made of materials of known densities is used to normalize CT image intensity values to estimate bone density. The process and system controls the speed, cutter engagement, orientation, and shape of the cavity so produced based on the normalized bone density values.

9 Claims, 4 Drawing Sheets

(51) Int. Cl.
G16H 30/40 (2018.01)
G16H 50/50 (2018.01)
A61B 6/03 (2006.01)
A61B 17/17 (2006.01)
A61F 2/46 (2006.01)
A61B 34/20 (2016.01)
A61B 90/00 (2016.01)

(52) U.S. Cl.
CPC ............ A61B 34/30 (2016.02); A61F 2/46 (2013.01); G16H 30/40 (2018.01); G16H 50/50 (2018.01); A61B 2034/104 (2016.02); A61B 2034/105 (2016.02); A61B 2034/2055 (2016.02); A61B 2090/3762 (2016.02); A61F 2002/4633 (2013.01)

(56) References Cited

U.S. PATENT DOCUMENTS

| | | | |
|---|---|---|---|
| 6,990,222 B2* | 1/2006 | Arnold | A61B 5/02007 378/18 |
| 8,649,577 B1 | 2/2014 | Arnold et al. | |
| 2010/0086181 A1* | 4/2010 | Zug | A61F 2/46 382/128 |
| 2011/0306985 A1* | 12/2011 | Inoue | G06T 15/08 606/130 |
| 2012/0059378 A1 | 3/2012 | Farrell | |
| 2013/0035690 A1 | 2/2013 | Mittelstadt | |
| 2014/0376701 A1* | 12/2014 | Kopperdahl | A61B 6/582 378/207 |
| 2015/0348259 A1* | 12/2015 | Souza | G06T 7/11 382/131 |
| 2019/0209331 A1* | 7/2019 | Varadarajan | A61F 2/30 |

OTHER PUBLICATIONS

Sande, Erlend Peter Skaug, "Interphantom and interscanner variations for Hounsfield units—establishment of reference values for HU in a commercial QA phantom", Physics in Medicine and Biology, Aug. 16, 2010, pp. 5123-5135, vol. 55, Copyright Institute of Physics and Engineering in Medicine (2010); doi: 10.1088/0031-9155/55/17/015.

International Search Report dated May 4, 2016 for International Application No. PCT/US2016/013343 filed Jan. 14, 2016.

* cited by examiner

IMAGE AND LASER GUIDED CONTROL OF CUTTING USING A ROBOTIC SURGICAL SYSTEM

CROSS REFERENCE TO RELATED APPLICATIONS

This application claims priority benefit of U.S. Provisional Application Ser. No. 62/103,945 filed 15 Jan. 2015; the contents of which are hereby incorporated by reference.

FIELD OF THE INVENTION

The present invention in general relates to the field of computer assisted orthopedic surgery; and in particular to a new and useful process and system for planning and executing the creation of a cavity for a prosthesis into a bone based on clinical preferences and patient pre-operative image data.

BACKGROUND OF THE INVENTION

Joint replacement surgery is a commonly performed procedure to relieve pain and restore the function of a patient's degenerated joint. The position, orientation and compliance of the prosthetics implanted into the joint are critical factors that have a significant effect on the clinical outcome of the patient. Therefore, computer assisted surgical devices are gaining popularity as a tool to pre-operatively plan and precisely execute the plan to ensure an accurate final position and orientation of the prosthetics within the patient's bone that can improve long term clinical outcomes and increase the survival rate of the prosthesis. In general, the computer assisted surgical systems include two components, an interactive pre-operative planning software program and a computer assisted surgical device that utilizes the pre-operative data from the software to assist the surgeon in precisely executing the procedure.

The conventional interactive pre-operative planning software generates a three dimensional (3-D) model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to place the components of a desired prosthesis to the 3-D model of the boney anatomy to designate the best fit, position and orientation of the prosthesis to the bone. The user can then save this pre-operative planning data to an electronic medium that is loaded and read by a surgical device to assist the surgeon intra-operatively in executing the plan.

Figure 1:
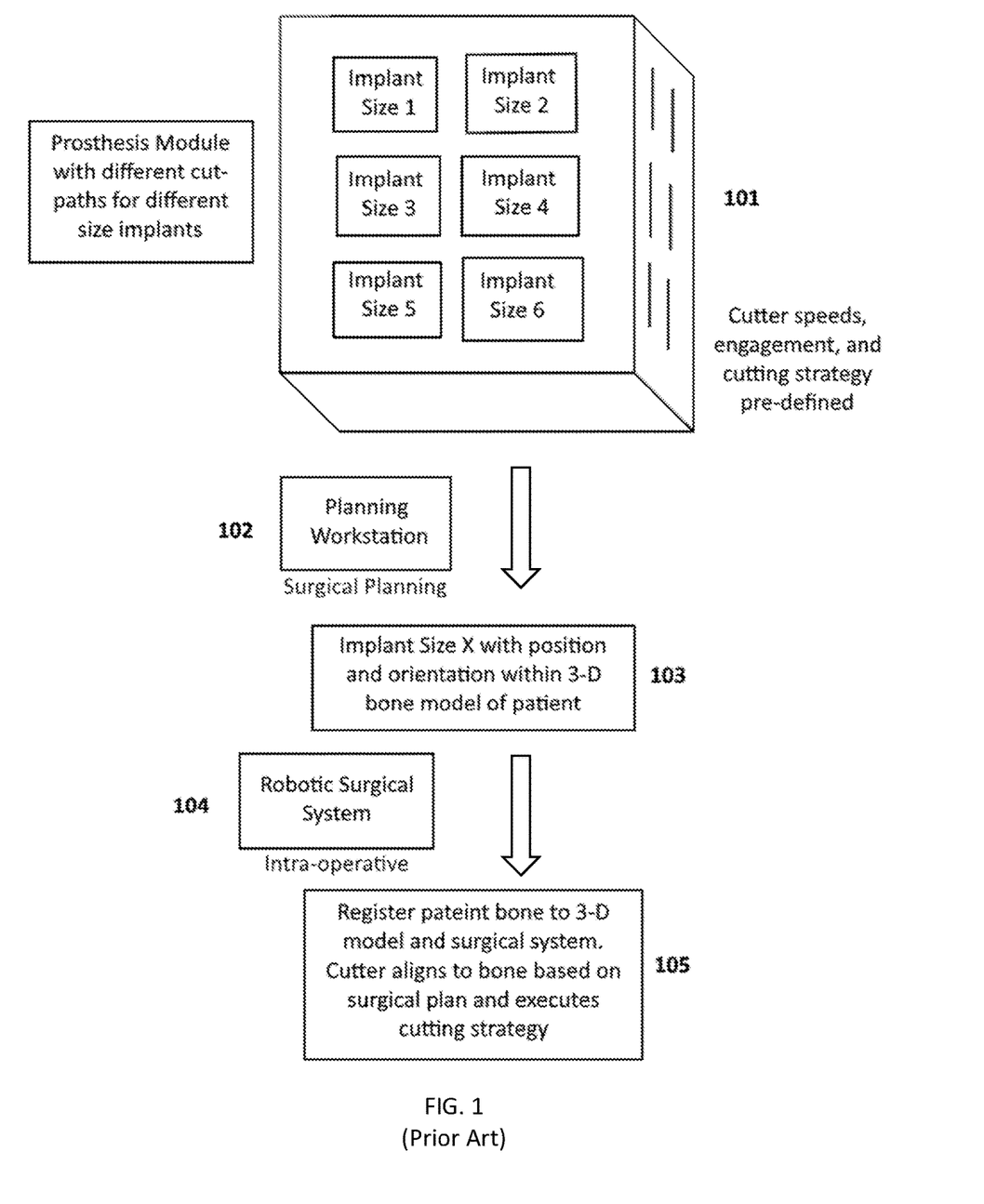
FIG. 1 depicts a prior art flowchart of a computer assisted surgical device to plan and execute the creation of a cut cavity to receive a prosthesis.

In certain prior art systems, with reference to FIG. 1, a cutting strategy or set of instructions to create a cavity is pre-defined, validated and fixed for a given manufacturers prosthesis module 101. The fixed parameters for a prosthetic cutting strategy includes the cutter tool orientations, the cut paths, cut volume, cutting speed, and cutting orientations that are dependent on the size and dimensions of the prosthesis in the manufacturer's prosthesis module. A surgeon with the use of a planning workstation 102 and a 3-D model of the patient's bone positions and orients the appropriate prosthetic in the desired location 103. Intra-operatively, the data is transferred to a computer assisted surgical system 104 and the patient's bone is registered to the 3-D model and surgical system that indicates to the surgical device where to start cutting in relation to the bone to obtain the desired position and orientation of the prosthesis when implanted 105. Although the fixed parameters ensure reproducibility of the cut volume for a given prosthesis, these conventional systems limit the ability of a surgeon to plan for other clinical factors depending on other clinical needs. For example, the surgeon may want to adjust a fixed parameter as to protect or decrease the amount of bone removed in a certain anatomical location or to accommodate an unexpected bone density. Additionally, the surgeon may want to specify a different position and orientation of the cutting tool based on the surgeons surgical approach, the amount of surgical access, exposure of the surgical area that may be dependent on a patient's body mass index (BMI) or other clinical priorities.

Additionally, one of the main goals of computer assisted surgery is to define a patient specific plan and precisely execute the procedure, in a timely manner, on a patient. The accuracy of the cut volume for a given implant is critical and errors can accumulate based on registration error, cutter manufacturing tolerances and implant manufacturing tolerances. Registration techniques well known in the art such as point to surface registration can align the coordinate frames of a patient's bone to the coordinate frames of a 3-D model of a patient's bone and to the coordinate frame of the surgical device. The registration technique results in coordinate frames that are aligned within 1 mm; however that error is still propagated and affects the overall error of the system and the resulting cut-volume. Current safety strategies are used to stop cutting when the cutter encounters hard tissues that may indicate cutting outside of the prescribed cut volume by measuring the force on the end mill, however during milling of the softer tissue (trabecular bone) there are no monitoring techniques to ensure the accuracy of the cutting within the cut volume.

In addition to ensuring the accuracy of the system and optimizing the cut-paths with pre-operative CT values, the time required for a procedure can be reduced by using the estimated bone density to define a cutting speed and feed rate automatically in the pre-operative planning stage. Since the cutter speed and cutter engagement is dependent upon the density of the bone, these parameters can be defined for specific regions within the volume to be cut in the pre-operative planning software and those instructions transferred to the surgical device to be implemented intra-operatively. There have been processes proposed to use image intensities from pre-operative image data to estimate a patient's bone density to calculate optimized cutter speeds and feed rates to reduce operating times intra-operatively (see for example U.S. Patent Publication 20110306985 A1).

However, studies have shown that there can be significant variability between absolute CT values (Hounsfield units) between CT scanners and even different CT scanners from the same manufacturer (Sande, Erlend et al. Phys. Med. Biol. 55 (2010) 5123-5135). Therefore, the variability in CT values from different CT scanners can vary, even with the same CT scanning protocol. This variability will affect a corresponding cutting speed and feed rate on a case by case basis. Considering that different hospitals and practitioners will use the CT scanners that are available at their site, it makes it difficult to rely on the CT values from different scanners and accurately estimate a bone density of a patient. Additionally, different materials, designs and configurations of the components for a cutting system can change or vary between different systems that affect what materials and at what rates the cutting can be accomplished. For example, the cutter design, cutter stiffness, safety parameters, cutter size all affect the chip load, feed rate, and cutter speed for a given density of bone to be cut. As noted above, variations in CT values to estimate bone density must also be considered in planning a procedure.

Therefore, there exists a need to provide a process with a set of validated cutting strategies for a given implant module whereupon the process provides options that allow a user to adjust parameters to specify a cut path and cavity to receive a prosthetic. In this way, a user can accommodate clinical needs into the planned procedure. There is a further need to accurately calculate and/or monitor a patient's bone density to reduce the cutting time to create a cavity to receive a prosthetic for any cutting system and from any CT pre-operative imaging data. There further exists a need to use a more accurate assessment of bone density to produce a better bone interface with the prosthetic. There also exists a need to monitor the accuracy of a cut-path during cutting that can be accomplished by the surgical system. There also exists a need to improve the accuracy of the cut cavity due to variations in implant and cutter manufacturing tolerances.

SUMMARY OF THE INVENTION

A process for creating a cavity to receive a prosthetic is provided, where pre-operative imaging data of bone or other anatomical structures set to receive a prosthetic or to be operated on are segmented. The segmented pre-operative imaging data and a set of reference data points are supplied to a software program to obtain a set of estimated density values applied to a three dimensional (3-D) model of the bone or other anatomical structures. Subsequently, the 3-D model is supplied to surgical planning software and a computer assisted surgical device to form the cavity to receive the prosthetic.

A system that implements the process for creating a cavity to receive a prosthetic is provided, where the system includes a computer that stores surgical planning software and is electrically connected to a computer assisted surgical device for creating the cavity to receive the prosthetic.

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE INVENTION

The present invention has utility as a system and process to plan and execute a computer assisted orthopedic procedure, but more particularly to provide a user with a plurality of options to plan, execute and monitor the creation of a cavity to receive a prosthetic based on clinical needs and pre-operative imaging data. As a result an inventive system controls the speed, cutter engagement, orientation and shape of the cavity so produced.

It is to be understood that in instances where a range of values are provided that the range is intended to encompass not only the end point values of the range but also intermediate values of the range as explicitly being included within the range. By way of example, a recited range from 1 to 4 is intended to include 1-2, 1-3, 2-4, 3-4, and 1-4.

As used herein, a cutter refers to the end effector of a computer assisted surgical device capable of removing material such as bone. The cutter speed refers to the rotation of the cutter about the cutter longitudinal axis. The cutter engagement or cutter feed rate refers to the amount the cutter engages or plunges into a material such as bone. A cut-path refers to the directional movement of the cutter to remove material such as bone. The term cut volume refers to the amount of material to be removed such as bone. Additionally, it is to be understood that the terms implant, prosthesis and prosthetic as used herein are interchangeable.

The present invention allows a user to more specifically tailor an orthopedic surgical plan and more accurately execute the plan on a patient to patient basis. One specific advantage is the use of pre-operative imaging data to be used in the planning to reduce operating times as well as monitor a procedure to optimize a cut-path and to ensure the accuracy of the procedure for a bone or other anatomical structure. Other anatomical structures subject to prosthetic replacement illustratively includes a tooth, cartilage, a tendon, or an ocular structure. Additionally, the pre-operative imaging data can be normalized to a universal phantom to account for CT inter-scanner variability, surgical tool variability, and can be used to aid in planning surgical procedures where multiple data scans are taken at different times. Furthermore, by providing a system with additional options for a given prosthetic module, an optimal cutting path can be defined prior to surgery within the operating room that ultimately provides the best result for the patient as well as the user in terms of clinical need, time reduction, and accuracy, compared to the procedures detailed in prior art FIG. 1.

The following description of the preferred embodiments of the invention is not intended to limit the invention to these preferred embodiments, but rather to enable any person skilled in the art to make and use this invention. The invention described herein illustratively uses total hip arthroplasty as an example. Although total hip arthroplasty is one procedure that can benefit from the disclosed embodiments other surgical procedures can illustratively include surgery to the knee joint, hip joint, spine, shoulder joint, elbow joint, ankle joint, jaw, a tumor site, and joints of the hand or foot. Generally, surgical procedures of the mastoid and cochlea are disfavored for the present invention.

The following description of the preferred embodiments further makes reference to the use of a phantom as a tool to normalize CT image intensity values, known as Hounsfield units (HU), to estimate bone density. However, the use of the phantom is not a necessary element of the present invention. Relative CT image intensity values (HUs) without a phantom can be used to estimate relative bone density and can similarly be used to practice the invention and will be referenced throughout where appropriate.

Figure 2:
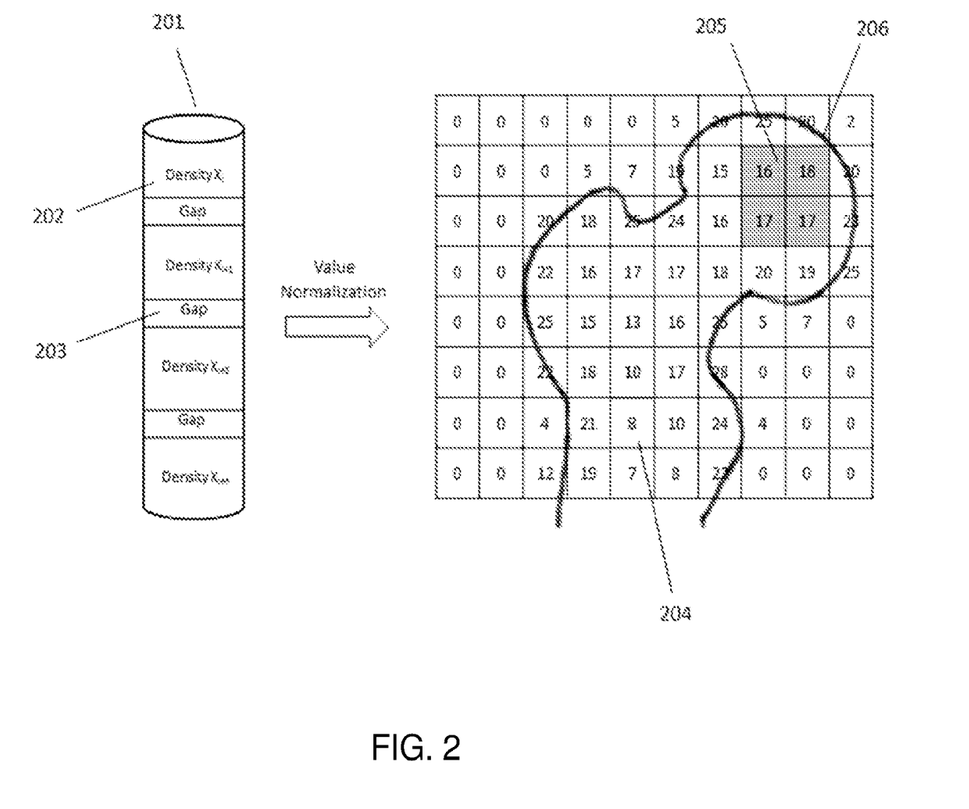
FIG. 2 shows an example of normalized CT-values of a patient with the use of a phantom to be used for planning and monitoring the creation of a cavity to receive a prosthetic.

One embodiment of the present invention, with reference to FIG. 2, includes a universal phantom 201 having different materials 202 of a known density within the phantom that is used with each CT or other imaging modality scan of a patient prior to a surgical procedure. In one embodiment, a gap is included between each of the materials to discern each of the materials in the case of imaging artifacts or a difference in reconstruction techniques that may cause blending of the imaging intensities. The materials used in the phantom have a known density that can be determined by modulus testing and other well-known techniques in the art. The different densities can be representative of different materials ranging from air to stainless steel. The Hounsfield unit Units (HU) has commonly been used as a measure of bone density with plenty of literature reporting a range of values that indicate a particular structure. Of particular importance, Hounsfield for trabecular and cortical bone has been measured in the range of 100-350 HU for fine trabecular bone, 350-700 HU for the porous crestal layer of cortical bone and trabecular bone, 700-1200 HU for crestal cortical bone and coarse trabecular bone and greater than 1200 HU for compact cortical bone. In one embodiment, the phantom 201 includes materials 202 with known densities that produce Hounsfield units within the range of 100 to 1200 HU. For example, one material has a density that produces Hounsfield units around 100 HU, while another produces HU at 200, and another material at 300 HU, etc.

By using a phantom with a material of known density, the HU produced from any CT scanner can be used as a reference to normalize and estimate the density of other objects within the scan such as bone or other anatomical structures. Since it is known that interscanner variability exists, even with the same operating parameters, the phantom can always be used as a reference to normalize other objects in the scan.

The use of a universal phantom as an imaging control allows a user to compensate for the unique imaging characteristics of a specific scanning device, as well as planning procedures based on scan data from different scanning devices. In a particular inventive embodiment, the scan data is from two or more scans. In one embodiment, the scans are each preferential in imaging soft and hard tissues, respectively or taken with temporal displacement on the same scanning device or disparate scanning devices. Data generated with a time lag between scans is used to predict degenerative and other changes in the bone of interest so as to improve prosthetic fit and fit retention longevity thereby extending the effective duration of the surgical procedure. Refinements as to soft tissue location and condition also provide more accurate input for planning of the surgical procedure. An exaggerated example of illustrative normalized and/or relative HUs of a patient's proximal femur 206 is shown in FIG. 2. The HU produced from the phantom and the corresponding known densities may be used to normalize the HU produced from the bone. In one inventive embodiment, interpolation may be used between varying HU units and densities of the phantom and the HU measured on the bone. In FIG. 2, illustrative normalized and/or relative values are shown, which represent a potential output of values for a voxel, represented as a box, according to different locations on the bone. In reality, the voxel size is much smaller and depends on the CT field of view and slice thickness. Generally, hard cortical bone makes up the outer surface of the bone. Trabecular or cancellous bone makes up the inner portion of the bone and is less dense than cortical bone. The amount of trabecular bone is greater within the femoral head, femoral neck, greater and less trochanter. The trabecular bone reduces in density and presence in the more central and distal regions. The dark grey area 205 represents more dense and abundant trabecular bone as indicated by the higher relative values. The light grey area 204 represents less dense and decrease in trabecular bone as indicated by the lower relative values. The highest values can be seen near the edge of the bone indicating hard cancellous bone. The numbers provided in the matrix are merely an example and are simply used to illustrate relative values at different locations within the bone. In reality, the hard cortical bone would have much higher HU values compared to the light grey box 204.

In a particular inventive embodiment, one or more phantoms may be used to account for any variations in HU values that may be present within the scanning field of view for a single scan. For example, a single phantom may be placed adjacent to a patient's leg, but cover the entire length of the scanning field of view. In another example, two or more phantoms may be placed around the patient so as to cover a greater area of the scanning field of view. Therefore, any variation in HU values within the scanning field of view may be accounted for and normalized to increase accuracy. In addition, many present day CT scanners utilize variable-dose scanning to improve resolution in critical regions, while reducing radiation in non-critical regions. Thus, in a particular embodiment, one or more phantoms may be used that have a constant density and is visible throughout the entire scan length.

The normalized CT values of the bone with the use of the phantom provides a means to use any CT scanner and any computer assisted surgical system to aid in planning and monitoring the cutting of a bone to receive a prosthesis. The use of relative CT values without normalization to a phantom permits the use of the invention without additional materials and computational time. In one embodiment of the invention, the pre-operative CT scan of the patient and with reference to the phantom is loaded into pre-operative planning software that builds a 3-D model of the bone using segmentation techniques well known in the art and performs the normalization of the HU values of the phantom with that of the HU values of the areas of interest of the patient. In other inventive embodiments, the pre-operative CT scan of the patient without reference to the phantom is loaded into pre-operative planning software that builds a 3-D model of the bone using segmentation techniques well known in the art. In one inventive embodiment, the HU values of the bone are correlated to density values using the HU values of the phantom with the known material densities. In another embodiment, when the phantom is not present, the pre-operative planning software segments the bone with the relative HU values imbedded in the 3-D model. Therefore, the 3-D model provides topology data as well as voxel data corresponding to bone density and/or relative bone density to be used with the surgical planning software and computer assisted surgical device.

Figure 3:
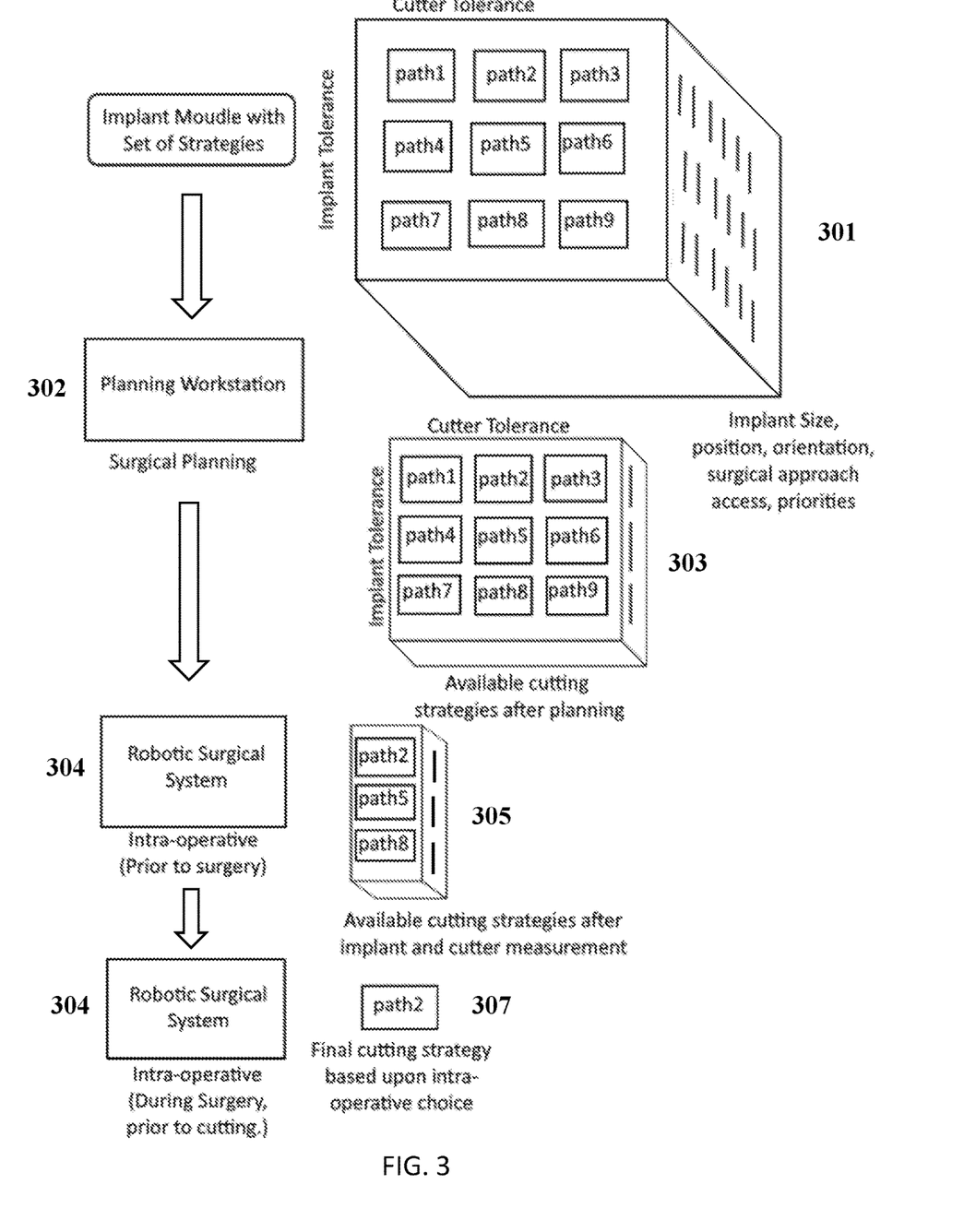
FIG. 3 depicts a flowchart of the present invention with a plurality of cutting strategies based on patient pre-operative imaging data, user input based on clinical need, and cutter and prosthetic tolerance measurements.
Figure 4:
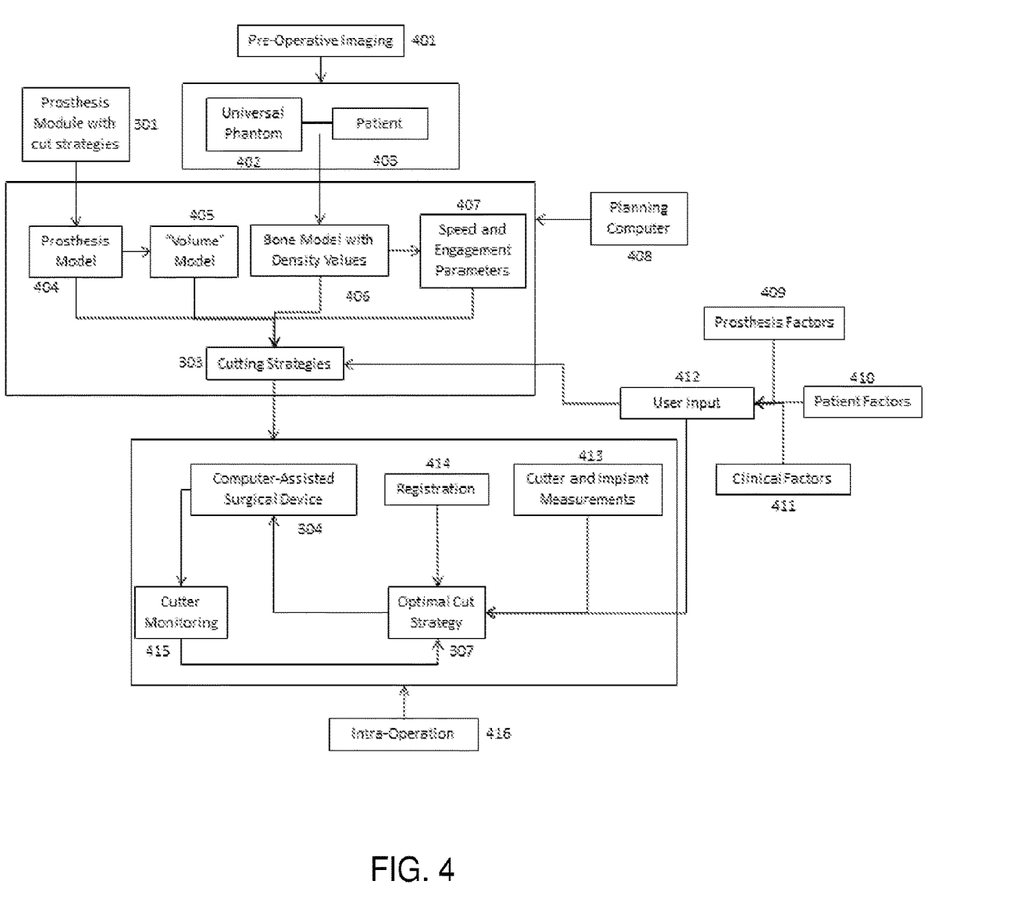
FIG. 4 is a flowchart illustratively outlining the systems and processes of the present invention.

Referring to FIGS. 3 and 4, the pre-operative imaging 401 of a patient 403 is loaded into a pre-operative planning computer 408 with or without the phantom 402. In one embodiment, a set of pre-validated cutting strategies 301 for a manufacturer's prosthesis module are loaded or are pre-loaded in the planning computer. The cutting strategies can have a plurality of options for a user to choose from to plan a procedure. Available cutting strategies illustratively include cut-paths to create cut volumes for different prosthesis sizes, geometries, shapes, function, and combinations thereof. Additionally, cut-paths available to create a cut volume illustratively include options for different cutter positions, orientations, cutter speeds, cutter types, cutter engagement, clinical needs, surgical approach, surgical access, clinical priorities, implant size tolerances, cutter size tolerances, and combinations thereof.

In one embodiment, the planning computer may use the uploaded pre-operative imaging data to create a 3-D model of the patient's bone. The 3-D model of the bone 406 includes the patient's bone topology as well as normalized and/or relative bone density information of the bone whereby normalization would be obtained through phantom scanning. In one embodiment, a user chooses the desired size of a prosthetic for a given patient 403. A prosthesis model 404 of the chosen implant is shown and can be manipulated by the user with the planning computer to optimally place the implant within the 3-D model of the bone 406. This is particularly well-suited for the implantation of prosthesis from a set of pre-made commercially available models that vary in size, geometry, materials, or a combination thereof. In another embodiment, a user can choose a prosthetic and it is automatically placed in the 3-D model of the bone 406 in what might be an optimal position and orientation. The user has full control to manipulate the prosthesis model 404 and the bone model 406 in the planning computer to place and orient the prosthesis as the user deems optimal. A user similarly has the ability to choose between different sizes of prosthetics to plan the procedure. Each size, geometry, shape, and function of a prosthetic within the prosthesis module has an associated cut volume or volume model 405 that further defines a sub-set of cutting strategies 303 that can be used to cut a volume of bone to receive a desired prosthesis. In some inventive embodiments, a pre-validated cutting strategy is provided for each of the pre-made prostheses. The pre-validated cutting strategies also employing subject bone topography and voxel data.

In another embodiment, the planning computer can automatically determine a further sub-set of cutting strategies based on the normalized and/or relative voxel density information to determine cutting speeds, cutter positions, cutter engagement speeds, and orientations that can reduce operating times or provide a least path of resistance while maintaining a cut volume that will precisely fit the prosthesis as specified for the user. A correlation can be made between density and a cutting system through experimental data or theoretical models by comparing forces experienced by an end-mill in different cutter positions, cutter orientations, cut-paths, cutter properties, cutting tools, while cutting different materials of known densities. For the illustrative example of total hip arthroplasty, the densities would be a correlation between forces and different densities of bone. The experimental data or theoretical models can be analyzed to make a correlation between HU values or density values and cutter speeds and cutter engagements. The correlation data can be loaded or is pre-loading into the planning computer. This is referred to as the speed and engagement parameters 407, which uses the normalized and/or relative density values and the bone topology to reference the experimental or theoretical data that estimate cutting speeds, cutter positions, cutter engagements, and cutter orientations before cutting and during cutting within the bone that can provide a least path of resistance or reduce operating times while maintaining a cut volume to precisely receive a prosthesis. A precision of within 5% is routinely obtained with the present invention. In specific embodiments cut precision is within 1%, while in still other embodiments within 0.5%. The speed and engagement parameters 407 define a further sub-set of cutting strategies 303 that can be used by the surgical device.

In another embodiment, with respect to cutting the femoral cavity to receive a prosthetic in total hip arthroplasty, the computer assisted device will cut the volume of the cavity prior to removing the femoral head. The region of the cut volume proximal of the osteotomy level is known as a pre-cut volume. The shape of the pre-cut volume is not of significant importance as it will be removed when the osteotomy is performed and as such can be performed quickly and with lower dimensional tolerances than the cut volume. The pre-cut volume determines the access, cutter positions, and cutter orientations to reach the important cutting of the shape that will receive the implant and functions as a starting geometry. The 3-D model with normalized and/or relative density values 406 and the speed and engagement parameters 407 may be used to define a sub-set of cutting strategies to optimize the pre-cut volume. In this inventive embodiment, a selected path of resistance may be determined from the density values, whereby the pre-cut volume allows for access to the more distal regions that will receive the prosthesis but will also reduce the cutting time of the pre-cut volume and thus the overall procedural time. It is appreciated that the selected path is often chosen to be a shortest, or minimal effort path, based on user selected values. Similarly, since the pre-cut volume includes cutting the hard cortical bone, the normalized and/or relative density values can determine the weakest points of the cortical bone in this volume, which can be related to a sub-set of cutting strategies with cutter speed, engagement, positions and orientations will reduce operating times and still create a volume to precisely receive a prosthesis in a position and orientation as specified by the user.

In another embodiment, a sub-set of cutting strategies 303 can be further defined from user input 412. For example, the size, shape, function of the prosthesis, noted as prosthesis factors 409 is defined by the user. The user input 412 can also include clinical factors 411. In one embodiment, clinical factors 411 can include a user's surgical approach to the procedure. For example, there are different surgical approaches in total hip arthroplasty such as posterolateral, direct anterior, etc. whereby the position and orientation of the starting position of the cutter can be adjusted by the user to accommodate that particular surgical approach. In one inventive embodiment, the surgical approach includes the removal of bone prior to cutting. For example, in the posterolateral approach the femoral head and neck is not removed prior to cutting and requires a pre-cut volume to be cut through the femoral head and neck. In the direct anterior approach, many surgeons will remove the femoral head prior to cutting which does not require a pre-cut volume to be cut through the femoral head and neck. Thus, the user input can define a sub-set of cutting strategies that specify if a pre-cut volume needs to be cut, or if the cutting can be optimized when no pre-cut is necessary. In another inventive embodiment, clinical factors include surgical access. For example a user can decide to choose a minimally invasive technique whereby a sub-set of cutting strategies with cut-paths, cutter position and cutter orientations that are less likely to interact with surrounding tissue or stay within the bound region of the minimally invasive incision or retracted tissue. In another inventive embodiment, clinical factors include surgical strategy or clinical priorities. For example, a user may desire to preserve bone in one region at the expense of cutting bone in another region. Illustratively, a patient may have significant muscle attachment to the greater trochanter, in which, one cutting strategy might endanger the muscle. A user may choose a sub-set of cutting strategies 303 with cutter position and cutter orientations that cut away from the muscle while still creating a cavity to precisely receive the prosthesis.

In another inventive embodiment, the user input can choose a sub-set of cutting strategies 303 that account for patient factors 410. For example, a patient with a high BMI provides less surgical access and exposure of the bone during surgery. By accounting for the patient's BMI, a sub-set of cutting strategies 303 can be specified by the user so the cut-paths, cutter positions, and cutter orientations can gain access to the bone, while minimizing soft tissue interaction with the ability to create a cavity to precisely receive the prosthesis as specified by the user. In one embodiment, the prosthesis model 404, volume model 405, bone model with normalized and/or relative density values 406, speed and engagement parameters 407, and user input 412 in terms of prosthesis factors 409, patient factors 410 and clinical factors 411 and any combinations thereof can all be used to define a sub-set of cutting strategies 303 from the prosthesis module cut strategies 301 on a patient to patient basis to create a cavity to precisely receive a prosthesis in a position and orientation as specified by the user. It is appreciated that a cutter according to the present invention experiences torsional forces that are different than those of a drill owing to a lack of physical constraint and variable cutting contacts.

Once a sub-set of cutting strategies 303 is defined from the pre-operative planning, the data with the different cut-strategies, cut-paths, cut-parameters, or a combination thereof are saved to an electronic medium to be transferred and used intra-operatively 416. In one embodiment, a computer that receives and reads the electronic medium is electrically connected to a computer assisted surgical device 304. In another embodiment the computer is in communication with a computer assisted surgical device wirelessly illustratively by WiFi, Bluetooth, optical communication, internet connection, or a combination thereof. In another embodiment a computer to receive and read the medium is incorporated within the computer-assisted surgical device. In another embodiment, the computer assisted surgical device receives and reads the electronic medium directly from the workstation 302.

Intra-operatively, the sub-set of cutting strategies 303 for the pre-operative planning may be further defined into a smaller set of cutting strategies 305 during registration of the bone, laser scans of the cutter and implant 413, and final user input to choose an optimal cutting strategy 307. In one embodiment, during the surgery, the cutter and implant may be removed from there sterile tray, and measured using a non-contact measurement scanning techniques. The measurement can be compared to the set of cutting strategies 303 and define a new sub-set of strategies 305 that will adjust the cutting volume defined based upon the actual measurement. The measurement assumes the cutter and implant manufacturing tolerance deviates from nominal and that the scanning accuracy of the non-contact measurement system is more accurate than the actual manufacturability of the cutter and the implant. Therefore the overall accuracy of the system is enhanced to a best match of the implant and cutter shape.

In another embodiment, a further sub-set of cutting strategies 305 may be defined during registration 414 of the patient's bone, to the 3-D model of the bone with the normalized and/or relative density information, and the surgical device. For example, registration techniques can be used to define the location or areas of soft tissue that may have been missed in the pre-operative images. Similarly, a patient's bone may contain several osteophytes that require removal or will affect the cut-path, whereby registering or digitizing the location of these features will define a new sub-set of cutting strategies 305 to account for these unforeseen objects.

In another embodiment final user input 412 is needed intraoperatively to choose a final optimal cut-strategy 307 for the patient 403. The user input 412 to choose the final strategy can similarly come from prosthesis factors 409, patient factors 410, clinical factors 411 and combinations thereof. For example, after making the incision to gain access to the surgical site, there may be less exposure of the bone then was anticipated. Therefore, from the sub-set of cutting strategies 305 will be the option to choose a cut-path 307 that accounts for the reduced exposure and will also have the parameters set in the pre-operative planning, the patient registration 414 and cutter and implant measurements 413 and any combinations thereof that creates a cavity to precisely receive a prosthesis.

Once the optimal cutting strategy 307 for the patient 403 is determined, the instructions are executed by the computer-assisted surgical device 304. In one embodiment, the 3-D bone model with the normalized and/or relative density values can be used and compared with forces measured by the cutter in real-time. In the case of using relative bone density values, once the cutter comes into contact with the bone, the force experienced by the cutter can be correlated to the relative density value at that initial position. Once the force of the cutter is correlated to at least one relative bone density value, the bias of any subsequent relative bone density value can be correlated with the force experienced by the cutter in real time. The comparisons can be utilized for many different functions.

In one embodiment, once the bone is exposed, the cutter speed has been reached and is in a safe position ready to cut, the cutter can engage quickly to the bone, as the forces measured on the cutter will be negligible (cutting air) until it reaches the bone. During cutting, the forces are measured in real-time and monitor the cutting procedure 415. The forces experienced in real-time should similarly match the values expected from the patient's 3-D model with the normalized density values or with the differences in relative density values. The cutter monitoring 415 between the 3-D model and the forces experienced on the cutter can be used to ensure the accuracy of the cut. The cutter monitoring 415 between the 3-D model and the forces experienced on the cutter can ensure that the registration 414 was accurate to provide an additional safety mechanism. In one embodiment, the comparison of the real-time forces and 3-D density data may be shown in real-time to the user by way of a monitor, where the cutter is in relation to the bone and the progress of the procedure.

In another inventive embodiment, the cutter may experience forces that are outside of an expected range from the bone model density data and can indicate if the cutting is slightly outside of a specified cut-volume from the optimal cut strategy 307. Similarly, if the measured forces are really low, it may indicate that soft tissue or other critical anatomy is being cut. In these scenarios, the cutting is immediately halted or a signal or indication may be provided to the user by way of a monitor to pause the cutting and make sure the cutter position and orientation is in the prescribed cut-path. A monitor can provide the user with a graphic of the position and orientation the cutter should be in based on the optimal cut strategy defined pre-operatively with where the cutter position and orientation is in real-time. In one embodiment, during this pause and the comparison of the plan with the real-time position and orientation of the cutter will allow the user to provide input from a set of options to adjust the position and orientation of the cutter, or the cut strategy in general that will still finish the cut cavity to precisely receive the prosthesis.

In another inventive embodiment, the cutter monitoring 415 using the real-time force feedback and the 3-D density values can automatically update the optimal cutting strategy 307 if the comparisons are outside a specific range. A learning algorithm can be used to change the cutter positions and orientations slightly that constantly improve the cut-path, whereby the real time forces and the 3-D density values continually become more matched with the changes. Therefore the system checks its own accuracy through this comparison and makes the slight changes to optimize the cut strategy 307 in real-time that results in a cavity to precisely receive the prosthesis in the desired position and orientation as specified by the user.

In another embodiment, the normalized and/or relative CT values can be used to aid in planning and executing revision surgeries. The bone density information could be used to infer the location of cement vs. bone and reduce the amount of bone removed in the process of removing cement. For example, during revision surgery, the surgeon may first remove the implant from the patient. Subsequently, using a scanner adapted for use in the operating room (OR), the patient will be scanned. From the scanner output, the bone/cement density map of the regions of interest can be created and that map will be used to remove all of the cement, infection, and bone as needed. These maps could be used so all of the cement was in fact removed from the patient and that a successful revision surgery was completed.

The advantages of the present invention disclosed herein are to optimize the cutting instructions and the cavity to create a higher quality implementation of the design philosophy for the cavity. The results will lead to more efficient cutting, which in turn translates into lower operating times. This approach also tailors the surgery for each patient and surgical philosophy without requiring dynamic cut-path validation.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The foregoing description is illustrative of particular embodiments of the invention, but is not meant to be a limitation upon the practice thereof. The following claims, including all equivalents thereof, are intended to define the scope of the invention.

The invention claimed is:

1. A process for creating a cavity to receive a prosthesis, said process comprising:
   segmenting pre-operative imaging data of a bone in a pre-operative planning software program to build a three dimensional (3-D) model of the bone comprised of voxels, each of said voxels having a normalized or relative estimated bone density value as determined by the pre-operative imaging data;
   providing a set of pre-validated cutting strategies in the pre-operative planning software program, wherein each of the set of pre-validated cutting strategies has instructions for a computer-assisted surgical device to cut the bone to receive the prosthesis;
   planning a type, size, and position for a prosthesis model relative to the 3-D model of the bone;
   determining a sub-set of pre-validated cutting strategies from the set of pre-validated cutting strategies based on the type and size of the prosthesis model;
   determining at least one final pre-validated cutting strategy from the sub-set of pre-validated cutting strategies based on the normalized or relative estimated bone density values in the 3-D bone model in relation to the planned position for the prosthesis model relative to the 3-D bone model; and
   transferring said at least one final pre-validated cutting strategy to the computer assisted surgical device, wherein said computer-assisted surgical device executes the at least one final pre-validated cutting strategy to form the cavity to receive the prosthesis;
   wherein the surgical planning software automatically determines the at least one final pre-validated cutting strategy based on the normalized or relative estimation of bone density values to determine cutting speeds, cutter positions and orientations that reduce operating times or provide a least path of resistance while maintaining a cut volume that will precisely fit the prosthesis.

2. The process of claim 1 wherein the sub-set of cutting strategies or the at least one final cutting strategy is further determined based on surgical access to the bone.

3. The process of claim 2 wherein the sub-set of cutting strategies or the at least one final cutting strategy is further determined based on a patient's BMI or presence of osteophytes.

4. The process of claim 3 wherein the surgical device uses an end miller cutter.

5. The process of claim 1 wherein the computer-assisted surgical device controls a cutter to cut the bone according to the at least one final cutting strategy, wherein the normalized or relative estimated density values are compared with forces measured on the cutter in real-time to monitor the cutter to ensure the accuracy of the cut with respect to said 3-D model.

6. The process of claim 5 wherein the forces measured on the cutter and the normalized or relative estimated density values are used to automatically update the at least one final pre-validated cutting strategy if comparisons therebetween are outside a specific range.

7. The process of claim 1 further comprising scanning a phantom to serve as a reference on a scanner that also produced said pre-operative imaging data, said reference used to normalize and estimate the density of the bone and the other anatomical structures.

8. The process of claim 7 wherein said phantom is comprised of two or more materials having different densities.

9. The process of claim 8 wherein said two or more materials produce Hounsfield units (HU) within the range of 100 to 1200 HU when scanned.

* * * * *